United States Patent
Van Geloof

(10) Patent No.: US 11,000,252 B2
(45) Date of Patent: May 11, 2021

(54) DEVICE FOR VISUALIZING A 3D OBJECT

(71) Applicant: KONINKLIJKE PHILIPS N.V., Eindhoven (NL)

(72) Inventor: Martijn Van Geloof, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 759 days.

(21) Appl. No.: 15/507,553

(22) PCT Filed: Sep. 1, 2015

(86) PCT No.: PCT/EP2015/069952
§ 371 (c)(1),
(2) Date: Feb. 28, 2017

(87) PCT Pub. No.: WO2016/034583
PCT Pub. Date: Mar. 10, 2016

(65) Prior Publication Data
US 2017/0281111 A1    Oct. 5, 2017

(30) Foreign Application Priority Data
Sep. 2, 2014   (EP) .................................. 14183165

(51) Int. Cl.
*A61B 6/00* (2006.01)
*A61B 6/03* (2006.01)
(Continued)

(52) U.S. Cl.
CPC .............. *A61B 6/5223* (2013.01); *A61B 6/03* (2013.01); *G06T 19/00* (2013.01); *A61B 6/466* (2013.01);
(Continued)

(58) Field of Classification Search
CPC .......... G06F 3/011; G06F 3/017; G06F 3/033; G06F 3/0346; G06F 3/04883;
(Continued)

(56) References Cited

U.S. PATENT DOCUMENTS 6,842,175 B1 *  1/2005  Schmalstieg ........... G06F 3/011
                                                      345/427
2003/0001905 A1   1/2003  Kemkers
(Continued)

FOREIGN PATENT DOCUMENTS

| CN | 103345668 A | 10/2013 |
| EP | 1566772 A2 | 8/2005 |
| WO | 2005078666 A1 | 8/2005 |

OTHER PUBLICATIONS

Schmidt, Taly Gilat "What is Inverse-Geometry CT?", Journal of Cardiovascular Computed Tomography (2011) vol. 5, No. 3, pp. 145-148.
(Continued)

*Primary Examiner* — Baisakhi Roy

(57) ABSTRACT

A device for visualizing a 3D object includes a processor configured to provide an image in a 2D projection plane, and to project an initial 3D object from an initial plane with an inverse projection transformation in the 2D projection plane of the image to achieve an inverse 2D object. The inverse projection transformation is a projection transformation, where a vanishing point is at the other side of the 2D projection plane than the initial object. The processor is further configured to point-mirror the inverse 2D object to achieve a mirrored non-inverse 2D object, and to project the mirrored non-inverse 2D object back to the initial plane to provide a corrected 3D object. Further, the processor is configured to project the corrected 3D object again to the 2D
(Continued)

projection plane of the image to provide a final 3D object appearing to be non-inversely projected.

14 Claims, 4 Drawing Sheets

(51) Int. Cl.
  *G06T 19/00* (2011.01)
  *G06T 15/20* (2011.01)
(52) U.S. Cl.
  CPC ........ *G06T 15/205* (2013.01); *G06T 2210/41* (2013.01); *G06T 2219/008* (2013.01)
(58) Field of Classification Search
  CPC ......... G06T 15/205; G06T 19/00; A61B 6/03; A61B 6/5223
  See application file for complete search history.

(56) References Cited

U.S. PATENT DOCUMENTS

| | | | |
|---|---|---|---|
| 2009/0262111 A1* | 10/2009 | Simon | A61B 6/12 345/420 |
| 2010/0286995 A1 | 11/2010 | Pekar | |
| 2011/0107270 A1 | 5/2011 | Wang | |
| 2011/0137156 A1* | 6/2011 | Razzaque | A61B 18/1477 600/424 |
| 2012/0290976 A1 | 11/2012 | Lahm | |
| 2012/0293512 A1 | 11/2012 | Yang | |
| 2013/0002646 A1 | 1/2013 | Lin | |
| 2013/0093763 A1* | 4/2013 | Shinoda | G06T 15/20 345/419 |

OTHER PUBLICATIONS

"X-ray computed tomography", from Widipedia, 2014.

* cited by examiner

DEVICE FOR VISUALIZING A 3D OBJECT

CROSS-REFERENCE TO PRIOR APPLICATIONS

This application is the U.S. National Phase application under 35 U.S.C. § 371 of International Application No. PCT/EP2015/069952, filed on Sep. 1, 2015, which claims the benefit of EP Patent Application No. 14183165.1, filed on Sep. 2, 2014. These applications are hereby incorporated by reference herein.

FIELD OF THE INVENTION

The invention relates to a device for visualizing a 3D object, an X-ray imaging system for visualizing a 3D object, a method for visualizing a 3D object, and a computer program element for controlling such device and a computer readable medium having stored such computer program element.

BACKGROUND OF THE INVENTION

WO 2005/078666 (A1) discloses a real time user interaction with a deformable surface model and an image processing system for segmenting an object of interest in a three-dimensional image using deformable surfaces.

EP 1 566 772 A2 discloses an X-ray computed tomographic apparatus comprising a scanner to scan in a three-dimensional region of a subject by X-rays, a storing unit to store projection data acquired by the scanning, a reconstruction processing unit to generate volume data which corresponds to a three-dimensional region, based on the stored projection data, an MPR processing unit to generate slice image data relating to three-direction slice planes from the volume data, a displaying unit to display the slice image data together with a graphic element representing a reconstruction range, an operating unit to operate the graphic element, and a reconstruction processing unit to reconstruct tomographic image data which corresponds to the reconstruction range represented by the graphic element, based on the stored projection data.

In interventional procedures, X-ray is used to help the physician see what is happening inside a human body. Objects on an X-ray image are projected using inverse perspective. This means objects further away from the X-ray detector appear bigger than objects closer to the X-ray detector. 3D objects that a user can manipulate, such as a cutting or a clipping plane, may also be rendered using inverse perspective, such that they correspond to the anatomy on the X-ray image. However, manipulating these inverse perspective 3D objects may feel counter-intuitive for a user. For instance, a clipping plane in the inverse perspective rendered scene feels malformed for a human viewer. The clipping plane looks as if it's not aligned with the actual cutting plane on the anatomical structure. When a user tries to move the clipping plane to the back it feels as if it's moving to the front and vice versa.

SUMMARY OF THE INVENTION

Hence, there may be a need for an improved device for visualizing a 3D object, which allows an easier manipulating of 3D objects.

The problem of the present invention is solved by the subject-matters of the independent claims, wherein further embodiments are incorporated in the dependent claims. It should be noted that the aspects of the invention described in the following apply also to the device for visualizing a 3D object, the X-ray imaging system for visualizing a 3D object, the method for visualizing a 3D object, the computer program element, and the computer readable medium.

According to the present invention, a device for visualizing a 3D object is presented. The device for visualizing a 3D object comprises a processing unit. The processing unit is configured to provide an image in a 2D projection plane. The image may be an X-ray image e.g. showing an anatomical structure projected using inverse perspective. Inverse projection is a projection, wherein objects further away from a detector appear bigger than objects closer to the detector. This is in contrast to normal human sight, where objects further away appear smaller than closer objects.

The processing unit according to the invention is configured to project an initial 3D object from an initial plane with an inverse projection transformation in the 2D projection plane of the image to achieve an inverse 2D object. As stated above, inverse projection transformation is a projection transformation, wherein objects further away from a detector appear bigger than objects closer to the detector. In other words, inverse projection transformation is a projection transformation, wherein a vanishing point is at the other side of the 2D projection plane than the initial object.

The processing unit according to the invention is further configured to point-mirror the inverse 2D object to achieve a mirrored non-inverse 2D object. The processing unit is configured to project the mirrored non-inverse 2D object back to the initial plane to provide a corrected 3D object. The processing unit is configured to project the corrected 3D object again to the 2D projection plane of the image to provide a final 3D object appearing to be non-inversely projected.

As a result, a perspective projected 3D object is achieved in an inverse perspective projected scene. In other words, it is described to reverse the inverse projection of a 3D object to be manipulated (e.g. a clipping plane) to a normal, non-inverse, perspective projection, while e.g. an anatomical structure in the image is maintained inversely projected.

By reversing the inverse projection of the 3D object to a normal, non-inverse, perspective projection while the anatomical structure in the image remains in inverse perspective, the user can easily manipulate the 3D object. The user can use and manipulate the 3D object naturally and intuitively as if it is seen with the human eye.

The invention is applicable to X-ray imaging modalities because of the inverse perspective projection of X-ray. As stated above, the image can therefore be an X-ray image. However, the invention can also be applied to any other imaging modality resulting in inverse perspective projected images.

As also stated above, the image may further comprise at least one inversely projected anatomical 3D structure, which remains inversely projected while providing the final object appearing to be non-inversely projected.

The image further comprises above explained initial 3D object. The initial 3D object can be understood as invertible object. In an example, the initial 3D object lies in the initial plane and has a shape symmetrical to the initial 3D object's geometrical centroid.

In an example, the initial 3D object is a cutting plane, a clipping plane or the like. This plane may be a plane that "cuts" one part of a 3D anatomical representation from another part of the 3D anatomical representation. The initial plane, in which the initial 3D object lies, can therefore be also understood as cutting plane. The clipping plane can be used e.g. in live screen where 3D CT/MR/rotational X-ray anatomy is overlayed on top of live X-ray images.

In an example, the device for visualizing a 3D object comprises an interface unit configured for a display and a manipulation of the initial 3D object. The interface unit may be a display with manipulation control and measurement tool. The cutting plane can be visualized in the interface unit as e.g. a rectangular 3D shape. The rectangle may indicate how and where a user can manipulate the cutting plane. The user can e.g. rotate or move the plane by dragging it with a mouse.

In an example, the rectangle is rendered as if it is perspective projected while the anatomical structure in the image is maintained in inverse perspective. However, when the user moves the rectangle away from the camera, the rectangle will appear bigger instead of smaller. This can then be solved by scaling the rectangle such that it grows when moving towards the camera. In the example, the processing unit is therefore configured to scale the final 3D object such that it enlarges when approaching a camera. The result can then be rendered along with the rest of the image using inverse perspective projection.

According to the present invention, also an X-ray imaging system for visualizing a 3D object is presented. The X-ray imaging system comprises an image acquisition unit, a display unit, and a device for visualizing a 3D object as described above. The image acquisition unit is configured for acquiring an image to be provided by above described processing unit of the device for visualizing a 3D object. The display unit is configured to display a final 3D object provided by the above described processing unit of the device for visualizing a 3D object.

According to the present invention, also a method for visualizing a 3D object is presented. It comprises the following steps, not necessarily in this order:
- providing an image in a 2D projection plane. The image may be an X-ray image e.g. showing an anatomical structure projected using inverse perspective;
- projecting an initial 3D object from an initial plane with an inverse projection transformation to the 2D projection plane of the image to achieve an inverse 2D object. The initial 3D object may be a clipping plane. The inverse projection transformation is a projection, wherein a vanishing point is at the other side of the 2D projection plane than the initial object. In other words, the perspective lines are reversed;
- point-mirroring the inverse 2D object to achieve a mirrored non-inverse 2D object;
- projecting the mirrored non-inverse 2D object back to the initial plane to provide a corrected 3D object;
- projecting the corrected 3D object to the 2D projection plane of the image to provide a final 3D object appearing to be non-inversely projected;

As a result, a perspective projected 3D object is achieved in an inverse perspective projected scene. In other words, it is described to reverse the inverse projection of a 3D object to be manipulated to normal, non-inverse, perspective projection, while e.g. an anatomical structure in the image is maintained in inversely projected.

According to the present invention, also a computer program element is presented, wherein the computer program element comprises program code means for causing a device for visualizing a 3D object as defined in the independent device claim to carry out the steps of the method for visualizing a 3D object when the computer program is run on a computer controlling the device for visualizing a 3D object.

It shall be understood that the device for visualizing a 3D object, the X-ray imaging system for visualizing a 3D object, the method for visualizing a 3D object, the computer program element, and the computer readable medium according to the independent claims have similar and/or identical preferred embodiments, in particular, as defined in the dependent claims. These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
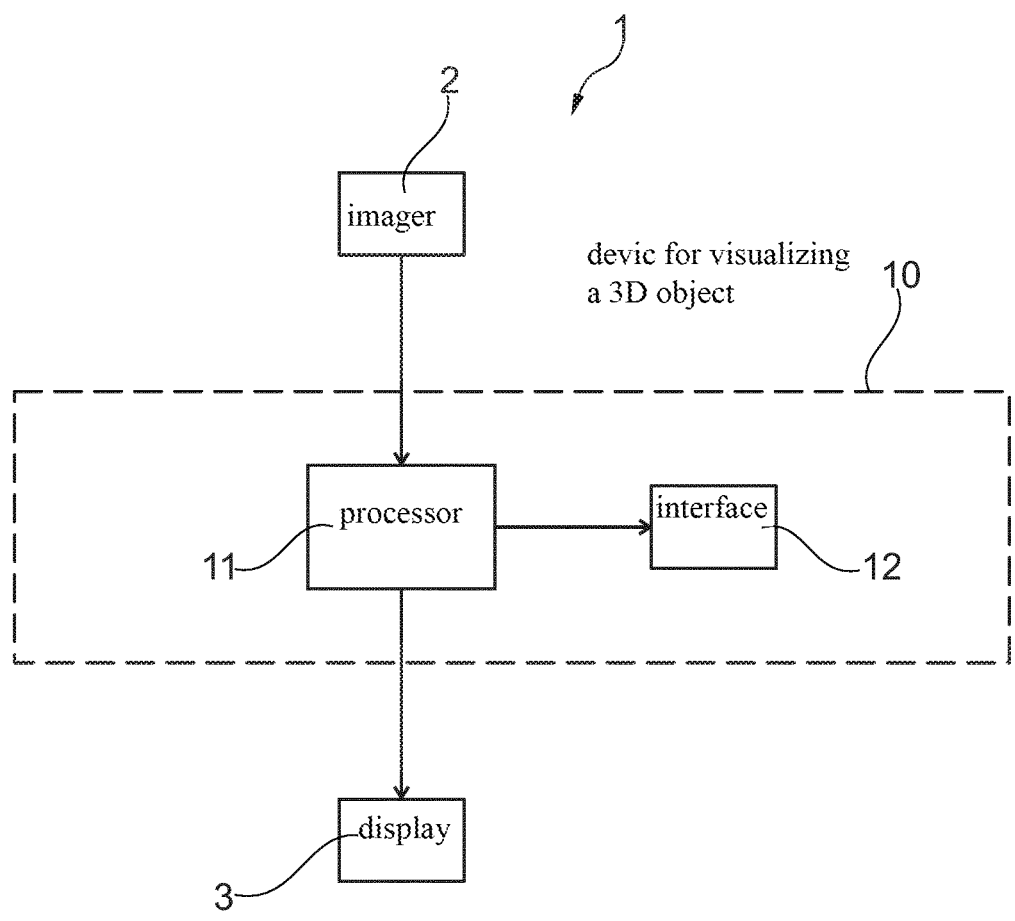
FIG. 1 shows a schematic drawing of an example of an embodiment of an X-ray imaging system 1 for visualizing a 3D object according to the invention.

FIG. 1 shows schematically and exemplarily an embodiment of an X-ray imaging system 1 for visualizing a 3D object according to the invention. The X-ray imaging system 1 comprises a device 10 for visualizing a 3D object, an image acquisition unit 2, and a display unit 3.

The device 10 for visualizing a 3D object comprises a processing unit 11. The image acquisition unit 2 acquires an image 20 to be provided by the processing unit 11 of the device 10 for visualizing a 3D object. The display unit 3 displays a final 3D object 28 (shown in FIG. 2) provided by the processing unit 11.

Figure 2:
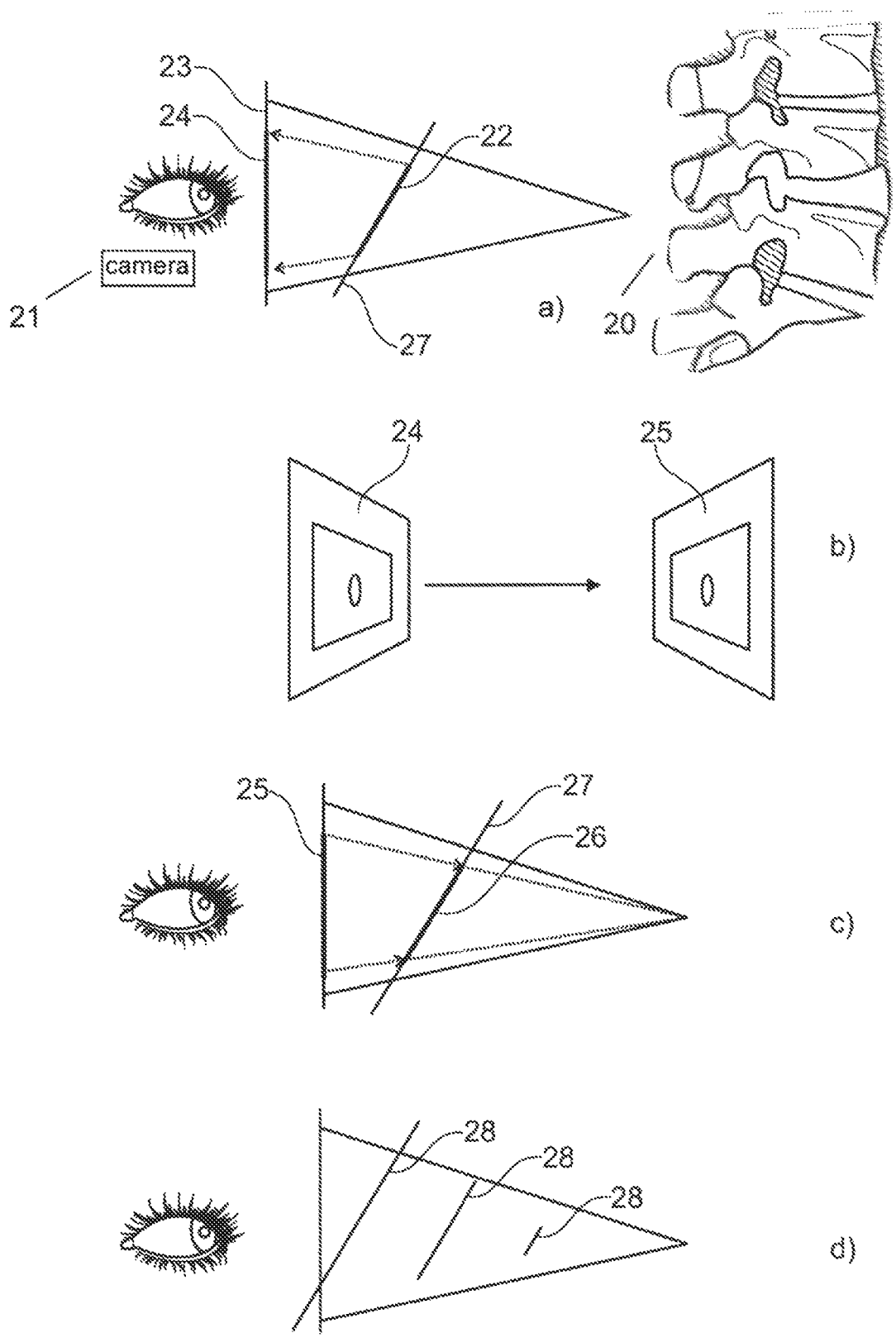
FIGS. 2a to d show schematically and exemplarily an embodiment of a visualization of a 3D object according to the invention.

The device 10 for visualizing a 3D object further comprises an interface unit 12 for a display and a manipulation of the initial 3D object 22 (shown in FIG. 2). The interface unit 12 may be the above described display unit 3 or a separate device.

The processing unit 11 of the device 10 for visualizing a 3D object provides an image in a 2D projection plane 23 (shown in FIG. 2). The image is here an X-ray image showing an inversely projected anatomical 3D structure. Inverse projection is a projection, wherein objects further away from a detector appear bigger than objects closer to the detector. This is in contrast to normal human life, where objects further away appear smaller than closer objects.

As shown in FIG. 2a, the processing unit 11 projects an initial 3D object 22 (here shown as 2D) in an initial plane 27 with an inverse projection transformation (shown by arrows) in a 2D projection plane 23 of the image to achieve an inverse 2D object 24. The initial 3D object 22 (shown in FIG. 2a as 2D) is a rectangular 3D shape that may cut a 3D anatomical structure into two parts. The rectangle may indicate how a user can manipulate the cutting plane. The initial 3D object 22 lies in the initial plane 27 and has a shape symmetrical to the initial 3D object's geometrical centroid. As stated above, inverse projection transformation is a projection transformation, wherein objects further away from a detector appear bigger than objects closer to the detector. In other words, inverse projection transformation is a projection transformation, wherein a vanishing point is at the other side of the 2D projection plane 23 than the initial object 22.

As shown in FIG. 2b, the processing unit 11 point-mirrors (shown by an arrow) all points of the inverse 2D object 24 to achieve a mirrored non-inverse 2D object 25 that looks reversed. As shown in FIG. 2c, the processing unit 11 then projects the mirrored non-inverse 2D object 25 back to the initial plane 27 to provide a corrected 3D object 26. Then, the corrected 3D object 26 still aligns with the initial plane 27, but is now deformed such that projecting it back to the 2D projection plane 23 of the image using the inverse perspective projection results in a perspective projected final 3D object 28 appearing to be non-inversely projected.

As a result, a perspective projected final 3D object 28 is achieved in an inverse perspective projected scene. By reversing the inverse projection of the 3D object to normal, non-inverse, perspective projection while the anatomical structure in the image remains in inverse perspective, the user can easily manipulate the 3D object as if it is seen with the human eye.

In FIG. 2c, the final 3D object or rectangle 28 (here shown in 2D) in is rendered as if it is perspective projected while the anatomical structure in the image is maintained in inverse perspective. However, when the user moves the rectangle 28 away from a user+s eye or a camera 21, the rectangle 28 will appear bigger instead of smaller. As shown in FIG. 2d, this can then be solved by scaling the rectangle 28 such that it grows when moving towards the user or the camera 21. The processing unit 11 therefore scales the final 3D object 28 such that it enlarges when approaching the user or the camera 21. The result can then be rendered along with the rest of the image using inverse perspective projection.

Figure 3:
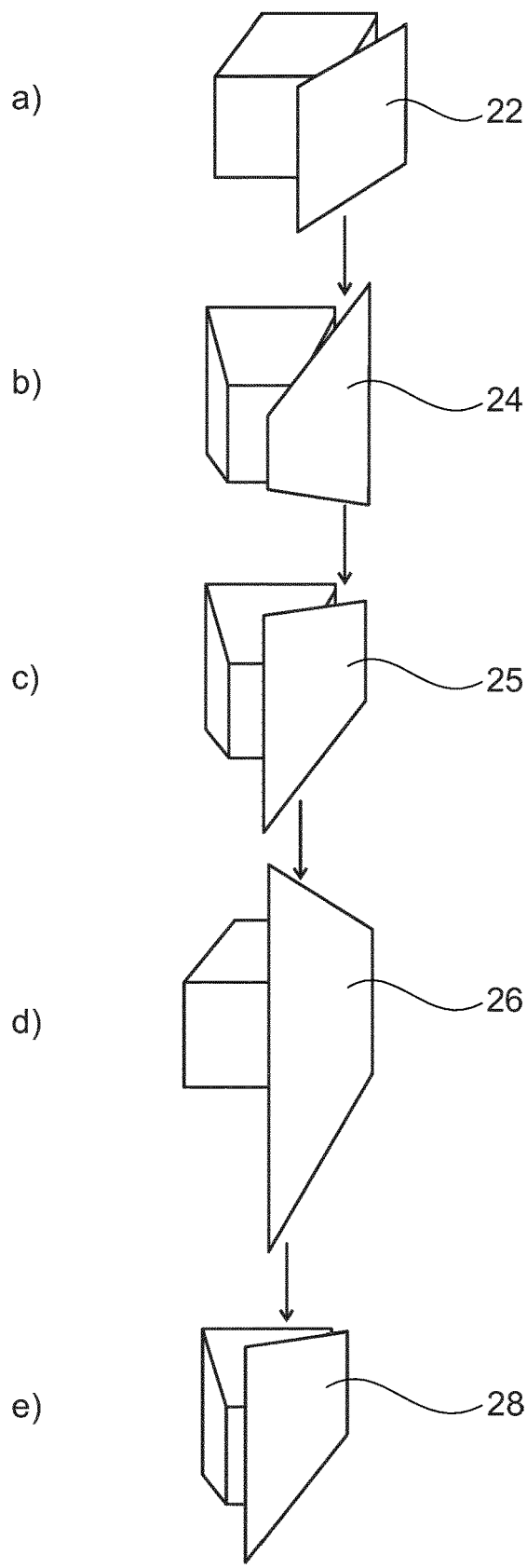
FIGS. 3a to e show schematically and exemplarily an embodiment of a visualization of a 3D object according to the invention.

FIG. 3a shows the initial 3D object 22 in parallel 2D projection and inversely projected to achieve the inverse 2D plane 24 shown in FIG. 3b. The inverse 2D plane is point-mirrored to achieve a point-mirrored non-inverse 2D plane 25, which makes the plane look perspective projected as shown in FIG. 3c. The point-mirrored non-inverse looking 2D plane 25 is then projected back to the original 3D plane to provide the corrected 3D object 26 shown in FIG. 3d in parallel projection. As shown in FIG. 3e, the corrected object is then rendered using perspective projection resulting in an image with an inverse perspective projection for a cube and a perspective projection for the final 3D object 28.

Figure 4:
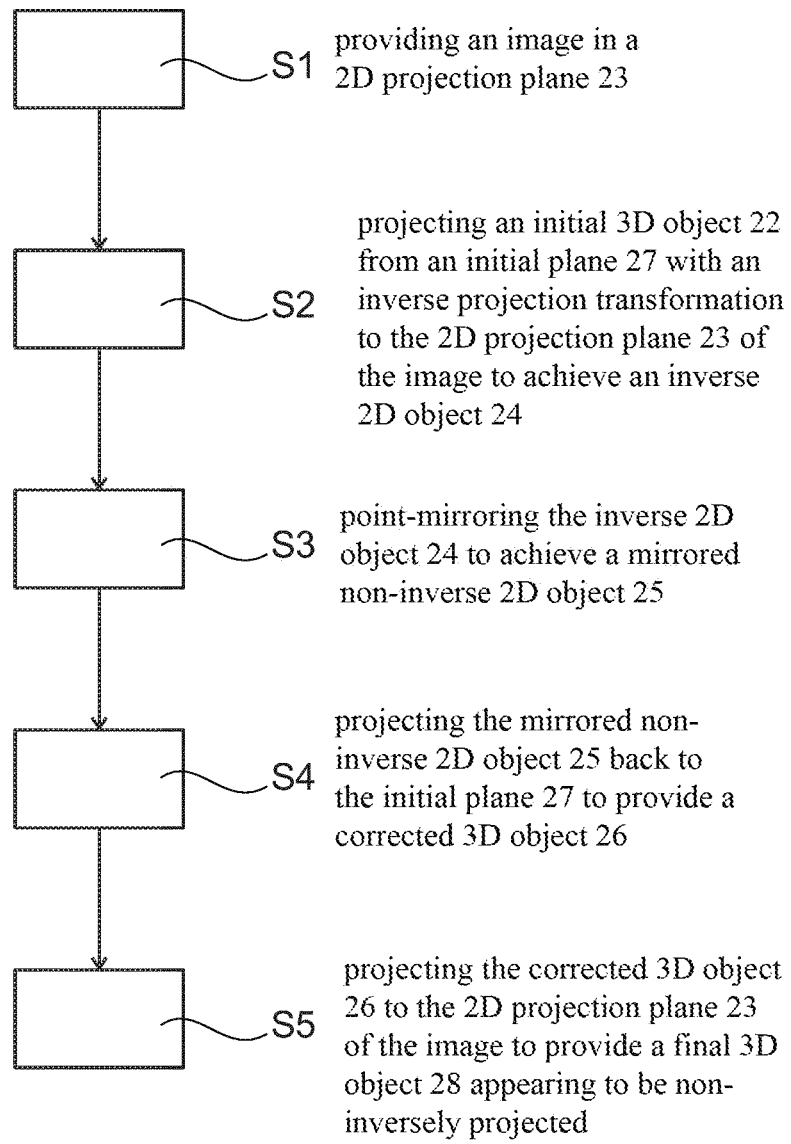
FIG. 4 shows basic steps of an example of a method for visualizing a 3D object.

FIG. 4 shows a schematic overview of steps of a method for visualizing a 3D object. The method comprises the following steps, not necessarily in this order:
  providing (S1) an image in a 2D projection plane 23;
  projecting (S2) an initial 3D object 22 from an initial plane 27 with an inverse projection transformation to the 2D projection plane 23 of the image to achieve an inverse 2D object 24. The inverse projection transformation is a projection, wherein a vanishing point is at the other side of the 2D projection plane 23 than the initial object;
  point-mirroring (S3) the inverse 2D object 24 to achieve a mirrored non-inverse 2D object 25;
  projecting (S4) the mirrored non-inverse 2D object 25 back to the initial plane 27 to provide a corrected 3D object 26;
  projecting (S5) the corrected 3D object 26 to the 2D projection plane 23 of the image to provide a final 3D object 28 appearing to be non-inversely projected.

As a result, a perspective projected 3D object is achieved in an inverse perspective projected scene. In other words, it is described to reverse the inverse projection of a 3D object to be manipulated (e.g. a clipping plane) to normal, non-inverse, perspective projection, while e.g. an anatomical structure in the image is maintained in inversely projected.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, all features can be combined providing synergetic effects that are more than the simple summation of the features.

While the invention has been illustrated and described in detail in the drawings and foregoing description, such illustration and description are to be considered illustrative or exemplary and not restrictive. In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for visualizing a 3D object, comprising a processor,
wherein the processor is configured to:
provide an image in a 2D projection plane;
overlay an initial 3D object lying in an initial plane on top of the image;
project the initial 3D object lying in the initial plane with an inverse projection transformation in the 2D projection plane of the image to achieve an inverse 2D object, wherein the initial 3D object has a shape symmetrical to the initial 3D object's geometrical centroid, wherein the inverse projection transformation is a projection transformation, wherein the initial 3D object has an initial vanishing point at a first side of the 2D projection plane and wherein the inverse 2D object has a vanishing point at a second side of the 2D projection plane opposite the first side;
point-mirror the inverse 2D object to achieve a mirrored non-inverse 2D object in the 2D projection plane;
project the mirrored non-inverse 2D object back to the initial plane to provide a corrected 3D object; and
project the corrected 3D object to the 2D projection plane of the image to provide a final 3D object appearing to be non-inversely projected.

2. The device according to claim 1, wherein the image is an X-ray image.

3. The device according to claim 1, wherein the initial D object is a cutting plane or a clipping plane.

4. The device according to claim 1, wherein the image further comprises an inversely projected anatomical 3D structure, which remains inversely projected while providing the final 3D object appearing to be non-inversely projected.

5. The device according to claim 4, wherein the processor is configured to scale the final 3D object such that it enlarges when approaching a camera.

6. The device according to claim 5, further comprising an interface configured to manipulate the initial 3D object.

7. An X-ray imaging system for visualizing a 3D object, comprising:
an imager configured for acquiring an image;
a processor configured to:
provide an image in a 2D projection plane;
overlay an initial 3D object lying in an initial plane on top of the image;
project the initial 3D object lying in the initial plane with an inverse projection transformation in the 2D projection plane of the image to achieve an inverse 2D object, wherein the initial 3D object has a shape symmetrical to the initial 3D object's geometrical centroid, wherein the inverse projection transformation is a projection transformation, wherein the initial 3D object has an initial vanishing point at a first side of the 2D projection plane and wherein the inverse 2D object has a vanishing point at a second side of the 2D projection plane opposite the first side;
point-mirror the inverse 2D object to achieve a mirrored non-inverse 2D object in the 2D projection plane;
project the mirrored non-inverse 2D object back to the initial plane to provide a corrected 3D object; and
project the corrected 3D object to the 2D projection plane of the image to provide a final 3D object appearing to be non-inversely projected; and
a display configured to display a final 3D object provided by the processor.

8. The X-ray imaging system for visualizing a 3D object of claim 7, wherein the image is an X-ray image.

9. The X-ray imaging system for visualizing a 3D object of claim 7, wherein the initial 3D object is a cutting plane or a clipping plane.

10. The X-ray imaging system for visualizing a 3D object of claim 7, wherein the image further comprises an inversely projected anatomical 3D structure, which remains inversely projected while providing the final 3D object appearing to be non-inversely projected.

11. The X-ray imaging system for visualizing a 3D object of claim 7, wherein the processor is configured to scale the final 3D object such that it enlarges when approaching a camera.

12. The X-ray imaging system for visualizing a 3D object of claim 7, further comprising an interface configured to manipulate the initial 3D object.

13. A method for visualizing a 3D object, comprising acts of:
providing an image in a 2D projection plane;
projecting an initial 3D object from an initial plane with an inverse projection transformation to the 2D projection plane of the image to achieve an inverse 2D object; wherein the initial 3D object has a shape symmetrical to the initial 3D object's geometrical centroid, wherein the inverse projection transformation is a projection, wherein the initial 3D object has an initial vanishing point at a first side of the 2D projection plane and wherein the inverse 2D object has a vanishing point at a second side of the 2D projection plane opposite the first side;
point-mirroring the inverse 2D object by a processor to achieve a mirrored non-inverse 2D object in the 2D projection plane;
projecting the mirrored non-inverse 2D object back to the initial plane to provide a corrected 3D object; and
projecting the corrected 3D object to the 2D projection plane of the image to provide a final 3D object appearing to be non-inversely projected.

14. A non-transitory computer readable medium comprising computer instructions which, when executed by a processor, configure the processor to perform a method for visualizing a 3D object, the method comprising:
providing an image in a 2D projection plane;
projecting an initial 3D object from an initial plane with an inverse projection transformation to the 2D projection plane of the image to achieve an inverse 2D object; wherein the initial 3D object has a shape symmetrical to the initial 3D object's geometrical centroid, wherein the inverse projection transformation is a projection, wherein the initial 3D object has an initial vanishing point at a first side of the 2D projection plane and wherein the inverse 2D object has a vanishing point at a second side of the 2D projection plane opposite the first side;
point-mirroring the inverse 2D object to achieve a mirrored non-inverse 2D object in the 2D projection plane;
projecting the mirrored non-inverse 2D object back to the initial plane to provide a corrected 3D object; and
projecting the corrected 3D object to the 2D projection plane of the image to provide a final 3D object appearing to be non-inversely projected.

* * * * *